(12) United States Patent
Nishiura et al.

(10) Patent No.: US 8,410,171 B2
(45) Date of Patent: Apr. 2, 2013

(54) ADHESIVE PREPARATION

(75) Inventors: Akio Nishiura, Mishima-gun (JP);
Hikaru Sugihara, Mishima-gun (JP);
Kazuya Abe, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 558 days.

(21) Appl. No.: 12/447,215

(22) PCT Filed: Oct. 25, 2007

(86) PCT No.: PCT/JP2007/070855
§ 371 (c)(1),
(2), (4) Date: Apr. 24, 2009

(87) PCT Pub. No.: WO2008/050848
PCT Pub. Date: May 2, 2008

(65) Prior Publication Data
US 2010/0041758 A1    Feb. 18, 2010

(30) Foreign Application Priority Data
Oct. 26, 2006 (JP) ................................. 2006-291634

(51) Int. Cl.
*A61K 31/557*    (2006.01)
(52) U.S. Cl. ....................................... 514/530; 424/426
(58) Field of Classification Search .................. None
See application file for complete search history.

(56) References Cited

U.S. PATENT DOCUMENTS
4,591,622 A    5/1986    Blizzard et al.
4,655,767 A    4/1987    Woodard et al.
7,547,715 B2 *  6/2009    Sakai et al. .................. 514/353
2004/0209848 A1 * 10/2004 Maruyama et al. ........... 514/102
2004/0258730 A1 * 12/2004 Tabata et al. .................. 424/426
2005/0020686 A1 *  1/2005 Maruyama et al. ........... 514/573

FOREIGN PATENT DOCUMENTS
| EP | 1424088 A1 * | 6/2004 |
| JP | 61-108681 A | 5/1986 |
| JP | 61-158920 A | 7/1986 |
| WO | 00/21542 A1 | 4/2000 |
| WO | 01/37877 A1 | 5/2001 |
| WO | 2006/118173 A1 | 11/2006 |

OTHER PUBLICATIONS

Roseman et al., Transport of Prostaglandins through Silicone Rubber, J. Pharm. Sci., vol. 70(5), May 1981, pp. 562-566.*
Roseman, T.J. et al., Transport of prostaglandins through silicone rubber., J Pharm Sci, 1981, Vo. 70, No. 5, p. 562-566.
Roseman, T.J. , Selectivity of silicone rubber toward prostaglandin permeability., J Pharm Sc, 1979, vol. 68, No. 2, p. 263-265.
Daukoningu Kabushiki Kaisha Medikaru Jigyobu, Yosuke Urabe, Silicone no DDS eno Oyo, DDS Gijutsu no Shinpo, Kabushiki Kaisha Yakugyo Jihosha, Nov. 22, 1990. pp. 193-206.
Extended European Search Report dated Jul. 31, 2012 issued by the European Patent Office in European Application No. 07830589.3.

* cited by examiner

*Primary Examiner* — Sreeni Padmanabhan
*Assistant Examiner* — Svetlana M Ivanova
(74) *Attorney, Agent, or Firm* — Sughrue Mion, PLLC (57) ABSTRACT

An adhesive preparation which has a pressure-sensitive adhesive layer comprising two components, i.e., a C1-4 alcohol ester of 4-{[2-((1R,2R,3R)-3-hydroxy-2-{(1E,3S)-3-hydroxy-4-[3-(methoxymethyl)phenyl]but-1-enyl}-5-osocyclopentyl)ethyl]sulfanyl}butanoic acid and a silicone-based pressure-sensitive adhesive. This is an effective and safe preparation which is stable, shows little change in skin permability and release a drug not rapidly but continuously.

18 Claims, 2 Drawing Sheets

ADHESIVE PREPARATION

TECHNICAL FIELD

The present invention relates to a sustained release adhesive preparation which is stable and shows a small change in drug skin permeability due to difference in application site or the like, comprising an adhesive layer containing two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid (may be abbreviated as "C1-4 alcohol ester" hereinafter) and a silicone adhesive.

BACKGROUND OF THE INVENTION

Prostaglandin (to be referred to as PG hereinafter)s are compounds which show strong activities with a very small amount by broadly distributing in various organs and body fluid in the living body and have a great variety of physiological activities such as relaxation and contraction of smooth muscle, contraction and dilation of blood vessel, platelet agglutination inhibitory activity and the like. Among PGs, since $PGE_2$ has physiological activities such as cell protective activity, uterine contraction, pain producing activity, acceleration of digestive tract peristalsis, awakening activity, a suppressive effect on gastric acid secretion, hypotensive activity and diuretic activity, and it has been used in the prevention and treatment of various diseases.

However, since PGs are chemically very unstable, their effective administration methods are limited to intravenous administration and the like and have a possibility of side effects such as expressing hypotension, gastroenteric disorder, skin blood vessel edema (*The Journal of Clinical Investigation*, vol. 108, pp. 25-30, 2001). 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid is a compound known as 5-thia-ω-substituted phenyl-prostaglandin E derivative having agonistic activity for EP4 which is one of $PGE_2$ receptor subtypes. It is useful for preventing and/or treating various diseases such as bone disease and the like (e.g., see Patent References 4 and 5). Not only the compound but also C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid is a very unstable compound. It is known that they change over time easily by the influences of heat, moisture, and the pH, etc. It is considered that when systemic administration such as oral administration or intravenous administration (e.g., rapid intravenous injection, intravenous drip infusion or the like) of the C1-4 alcohol ester is performed, the C1-4 alcohol ester is converted into an active form, and if the blood concentration of the active form rapidly increases, an influence on the cardiovascular system such as hypotension or an increase in heart rate or a side effect such as diarrhea or cutaneous angioedema may be caused. Further, in the case where a bone disease is treated, since bone formation takes a long time, it is necessary to administer a drug many times through intravenous administration and a burden is imposed on a patient, therefore, it is not necessarily satisfactory.

In view of this, novel administration route and dosage form of PGs have been studied. With regard to the novel administration route and dosage form of PGs for applying them to a bone disease, it has heretofore been known that the C1-4 alcohol ester can be used for preventing and/or treating bone loss disease by formulating it into a controlled release preparation (e.g., a microcapsule preparation, a microsphere preparation, a nanosphere preparation or the like) for local administration, or by dissolving it in an organic solvent along with a bioabsorbable polymer followed by lyophilization thereby to prepare an implantable sustained release film preparation for local administration (e.g., see Patent references 6 and 7). Further, it is disclosed that an EP1 agonist which is one of the $PGE_2$ receptor subtypes is percutaneously administered for increasing bone volume (e.g., see Patent reference 8). Further, it is disclosed that local administration of an EP4 receptor selective agonist is useful for the treatment of bone diseases (e.g., see Patent reference 9).

Further, as one of the novel dosage forms, a possibility of a percutaneous absorption preparation such as an adhesive preparation has also been studied (e.g., see Patent references 1, 2 and 3).

As for a characteristic of such an adhesive preparation, there is an advantage in that a burden to patients is reduced, for example, treatment can be performed at home, drug administration is not painful, the adhesive preparation can be removed easily after completion of medication, etc. However, due to the barrier function of the skin, percutaneous absorption of a drug is generally poor and it is often difficult to deliver a drug in an amount necessary for exhibiting the drug effect through the skin with a practical and limited applied area. Also, the adhesive preparation has many problems such as drug stability, sustainability, effect, safety (occurrence of side effects) and skin irritation (e.g., erythema, edema, itching, rash, pigmentation or the like). Many studies have been made for avoiding various problems of concern for such an adhesive preparation.

For example, it is known that depending on the compatibility of an additive (an amphiphilic solubilizer, a percutaneous absorption accelerator, a dermatological side effect relieving agent, a drug stabilizer and/or a crosslinking agent, or the like) or a filler to be incorporated in the adhesive preparation, the controlled release or acceleration of permeation of an active ingredient is adjusted, and the stability, percutaneous absorption or the like of a drug is improved.

As one example, Japanese patent No. 2655983 discloses a method of producing a percutaneous preparation with a matrix type structure or a storage tank type structure containing a main content layer obtained by mixing a drug mixture with a hydrophobic adhesive as a method of improving the stability of a drug having a tyrosinase inhibitory activity. It is described that the main content layer is a mixture of a hydrophobic adhesive, a percutaneous absorption accelerator for a drug, a drug stabilizer, a solubilizer for a drug in a system, and a dermatological side effect relieving agent (see Patent reference 10).

Further, it is disclosed that a percutaneous absorption preparation comprising a backing layer and an adhesive layer containing a drug, wherein the adhesive layer contains a mixed adhesive base having a hydrocarbon rubber and a silicon-containing polymer is excellent in percutaneous absorption of the drug in the preparation, and has low skin irritation and high stability of the drug over time (see Patent reference 11).

JP-A-5-238929 discloses a long-term sustained release preparation characterized in that a therapeutic agent for a metabolic bone disease is contained in silicone, and discloses that a substance for controlling the release rate of albumin or the like is used for controlling the release rate of a drug (see Patent reference 12).

When a plurality of additives are added thereto, the drug stability, percutaneous absorption and the like are improved, however, there is a concern that skin irritation or the like may be caused by the influence of the additives.

Further, as for 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid, a percutaneous absorption preparation for controlling blood concentration containing an ester thereof and a base for external preparations is disclosed. As the base for external preparations here, bases such as a styrene-isoprene-styrene block copolymer, an acrylate resin, and an acrylic copolymer resin are described (see Patent reference 13).

However, it was found that the percutaneous absorption preparation has a problem in the stability over time. That is, the drug is degraded while the preparation is being stored, therefore, there is a concern that a sufficient drug effect cannot be exhibited when it is used.

Further, in the case where a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid is used for a bone disease, particularly for bone fracture, since an affected area is immobilized in a cast, a drug cannot be applied to the affected area in some cases. Further, when an adhesive preparation is continue to be applied to the same area, itching or rash is caused in some cases. Moreover, depending on individual difference, difference in application site or the like, the drug concentration in the body becomes unstable. Therefore, there is a concern that, for example, the blood drug concentration rapidly increases and a very potent effect is exhibited or a side effect is exhibited. In order to avoid such a problem, an adhesive preparation which is not necessarily required to be applied to an affected area and is capable of exhibiting the same drug effect wherever in the body it is applied has been demanded. In order to achieve such a demand, an adhesive preparation with a small variation in drug skin permeability due to difference in application site, individual difference, the presence or absence of skin lesion such as injury or skin inflammation, etc., that is, an adhesive preparation with a small change in skin permeability is useful.

[Patent Reference 1] JP-A-58-134019
[Patent Reference 2] JP-B-07-25666
[Patent Reference 3] Japanese Patent No. 2910857
[Patent Reference 4] International Publication No. 00/003980
[Patent Reference 5] International Publication No. 01/037877
[Patent Reference 6] International Publication No. 03/009872
[Patent Reference 7] International Publication No. 03/041717
[Patent Reference 8] International Publication No. 00/051585
[Patent Reference 9] JP-A-2001-181210
[Patent Reference 10] Japanese Patent No. 2655983
[Patent Reference 11] JP-A-2006-16382
[Patent Reference 12] JP-A-05-238929
[Patent Reference 13] International Publication No. 06/118173

DISCLOSURE OF THE INVENTION

Problems that the Invention is to Solve

An object of the present invention is to provide an adhesive preparation in which an extremely chemically unstable C1-4 alcohol ester of 4-{[2-((1R,2R,3R)-3-hydroxy-2-{(1E,3S)-3-hydroxy-4-[3-(methoxymethyl)phenyl]but-1-enyl}-5-oxo-cyclopentyl)ethyl]sulfanyl}butanoic acid is stable and shows a small change in skin permeability. Further, another object of the present invention is to provide an adhesive preparation in which various problems of concern for adhesive preparations such as sustainability, effect, safety (occurrence of side effects), and skin irritation have been improved.

Means for Solving the Problems

The present inventors made intensive studies in order to achieve the above-mentioned objects, and as a result, they found that by preparing an adhesive preparation comprising an adhesive layer containing a combination of a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid and a specific silicone adhesive obtained by combining a polydimethylsiloxane which will be defined below with a silicate resin among a wide variety of silicone adhesives constituted by a silicone wax, a silicone oil, a silicone resin, a silicone elastomer, and/or a mixture thereof, degradation of the C1-4 alcohol ester is prevented and an adhesive preparation which is stable over time can be obtained, which could not be achieved by a combination of the C1-4 alcohol ester with an adhesive other than the silicone adhesive.

Further, the adhesive preparation of the present invention shows a small variation in drug skin permeability due to difference in application site, individual difference, the presence or absence of skin lesion such as injury or skin inflammation, etc., therefore, it is possible to prevent a rapid increase in blood drug concentration due to difference in application site, individual difference or the like and to avoid occurrence of side effects. Also, it was found that various problems of concern for adhesive preparations can be avoided by only 2 components, the C1-4 alcohol ester and the silicone adhesive without adding an additive such as a percutaneous absorption accelerator, a drug stabilizer or a dermatological side effect relieving agent which is usually added for adjusting the controlled release or acceleration of permeation of an active ingredient. Since the adhesive preparation of the present invention does not contain an additive other than the silicone adhesive, problems of concern in the case of adding a plurality of additives such as skin irritation can be avoided. Further, it was also found that since the adhesive preparation can provide controlled drug release and can release the drug in a sustained manner without providing rapid drug release and can sustain an effective concentration of the active form without causing a rapid increase in the blood concentration thereof, the drug effect can be exhibited in a sustained manner while avoiding side effects.

As described above, the present inventors found that the adhesive preparation of the present invention can achieve the above objects, and thus completed the present invention.

That is, the present invention relates to:

1. a sustained release adhesive preparation which is stable and has a low skin permeation rate ratio, comprising an adhesive layer containing two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl) ethyl]sulfanyl} butanoic acid and a silicone adhesive;

2. the preparation according to the above 1, wherein a concentration of the C1-4 alcohol ester is from 0.1% by mass to 5% by mass of the total of the adhesive layer;

3. the preparation according to the above 1, wherein a concentration of the C1-4 alcohol ester is from 10 μg/cm$^2$ to 500 μg/cm$^2$;

4. the preparation according to the above 1, wherein an area of the adhesive preparation is from 1 cm² to 100 cm²;

5. the preparation according to the above 1, wherein a thickness of the adhesive layer is from 20 μm to 150 μm;

6. the preparation according to the above 1, wherein the C1-4 alcohol ester is methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate;

7. the preparation according to the above 1, wherein a residual ratio of the C1-4 alcohol ester after storage at 40° C. for 1 month is 90% or more;

8. the preparation according to the above 1, wherein a skin permeation rate ratio for a stratum corneum-removed skin to that for a normal skin is from 1 to 5;

9. the preparation according to the above 1, wherein the silicone adhesive is:

[1] a mixture of a component (1): a linear or branched polydimethylsiloxane having a silanol group at a molecular chain end or in a side chain and a component (2): a polysilicate resin having a silanol group in the molecule;

[2] a condensation reaction product of the component (1) and the component (2); or

[3] a mixture of the mixture [1] and the condensation reaction product [2];

10. the preparation according to the above 9, wherein a viscosity of the component (1) at 25° C. is from 10 mPa·s to 100000 mPa·s and a weight average molecular weight of the component (2) in terms of styrene is from 500 to 100000;

11. the preparation according to the above 1, wherein the adhesive layer is produced by mixing a solution having a viscosity of from 1000 mPa·s to 10000 mPa·s obtained by adding 50 to 1000 parts by mass of an aromatic hydrocarbon organic solvent, an aliphatic hydrocarbon organic solvent, an ester organic solvent, or a mixed solvent thereof to 100 parts by mass of the silicone adhesive with the C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid as such or a mixture thereof with an aromatic hydrocarbon organic solvent, an aliphatic hydrocarbon organic solvent, an ester organic solvent, or a mixed solvent thereof;

12. the preparation according to the above 1 which is for the prevention, treatment and/or inhibition of progression of a bone disease;

13. the preparation according to the above 12, wherein the bone disease is bone fracture;

14. a sustained release adhesive preparation which is stable and has a low skin permeation rate ratio, comprising an adhesive layer containing two components, methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate and a silicone adhesive and satisfying the following conditions (1) to (6):

(1) a concentration of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate is from 0.1% by mass to 2% by mass of the total of the adhesive layer;

(2) a concentration of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate is from 10 μg/cm² to 200 μg/cm²;

(3) an area of the adhesive preparation is from 1 cm² to 25 cm²;

(4) a thickness of the adhesive layer is from 20 μm to 120 μm;

(5) a residual ratio of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate after storage at 40° C. for 1 month is 90% or more; and (6) a skin permeation rate ratio for a stratum corneum-removed skin to that for a normal skin is from 1 to 5;

15. the preparation according to the above 14, wherein the silicone adhesive is:

[1] a mixture of a component (1): a linear or branched polydimethylsiloxane having a silanol group at a molecular chain end or in a side chain and a component (2): a polysilicate resin having a silanol group in the molecule;

[2] a condensation reaction product of the component (1) and the component (2); or

[3] a mixture of the mixture [1] and the condensation reaction product [2];

16. the preparation according to the above 15, wherein a viscosity of the component (1) at 25° C. is from 10 mPa·s to 100000 mPa·s and a weight average molecular weight of the component (2) in terms of styrene is from 500 to 100000;

17. the preparation according to the above 14 which is produced by mixing a solution having a viscosity of from 1000 mPa·s to 10000 mPa·s obtained by adding 50 to 1000 parts by mass of an aromatic hydrocarbon organic solvent, an aliphatic hydrocarbon organic solvent, an ester organic solvent, or a mixed solvent thereof to 100 parts by mass of the silicone adhesive with methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate as such or a mixture thereof with an aromatic hydrocarbon organic solvent, an aliphatic hydrocarbon organic solvent, an ester organic solvent, or a mixed solvent thereof;

18. a method of stabilizing a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid contained in an adhesive preparation, wherein an adhesive layer in the adhesive preparation contains two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid and a silicone adhesive; and 19. a method of reducing a change in skin permeability of a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid contained in an adhesive preparation, wherein an adhesive layer in the adhesive preparation contains two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid and a silicone adhesive.

The C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoic acid contained in the adhesive preparation of the present invention is not limited in terms of its form (solid or liquid) or the like. When the C1-4 alcohol ester is formulated, the compound may be used as such or after dissolving it in an aromatic hydrocarbon organic solvent (e.g., benzene, toluene, xylene or the like), an aliphatic hydrocarbon organic solvent (e.g., pentane, hexane, heptane or the like), an ester organic solvent (e.g., ethyl acetate, butyl acetate or the like), or a mixed solvent thereof.

In the present invention, C1-4 alcohol ester of 4-{[2-((1R,2R,3R)-3-hydroxy-2-{(1E,3S)-3-hydroxy-4-[3-(methoxym- ethyl)phenyl]but-1-enyl}-5-oxocyclopentyl)ethyl]sulfanyl}butanoic acid is a compound represented by formula (I):

wherein ······ represents α-configuration, ⟋ represents β-configuration, R is C1-4 alkyl.

C1-4 alkyl represents methyl, ethyl, propyl, isopropyl, butyl, isobutyl, tert-butyl or sec-butyl (1-methylpropyl).

In the present invention, a preferable example of the compound represented by formula (I) includes the compound represented by formula (I-1):

wherein all symbols have the same meaning as described above, i.e. methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate etc.

In this connection, their naming was carried out using a computer program, ACD/NAME (registered trademark, Advanced Chemistry Development, Inc.), which mechanically produces IUPAC name.

According to the present invention, the compound represented by formula (I) is not limited to substantially pure and single substances and may contain impurities (e.g., by-products derived from production process, solvents, materials, degradation products and the like) as long as they are within the acceptable range as active ingredient of pharmaceuticals. The impurity content acceptable as active ingredient of pharmaceuticals varies depending on the impurities contained therein. In the case of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl} butanoate for example, it is preferable that the amount of each of the analogous substances as its degradation products is about 1.0% or less based on the entire amount, and total amount of the analogous substances is about 4.0% or less based on the entire amount.

The compound represented by formula (I) can be produced by using conventionally known methods, for example, the methods described in International Publication No. 00/003980, the method described in International Publication No. 03/009872, the method described in *Comprehensive Organic Transformations: A Guide to Functional Group Preparations*, Second Edition, (Richard C. La Roche John Wiley and Sons Inc, 1999) and the like, alone or by a combination of two or more thereof. Additionally, the thus produced compound can be purified by general purification means, for example, distillation under ordinal pressure or under a reduced pressure, a high performance liquid chromatography which uses silica gel or magnesium silicate or washing, recrystallization and the like.

The compound represented by formula (I) is metabolized when absorbed in the body and converted into 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid which is the active form. 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid is a compound represented by formula (I-A):

wherein all symbols have the same meaning as defined above.

The blood concentration of the active form when the compound represented by formula (I) is percutaneously administered as an adhesive preparation is not particularly limited as long as it is a concentration capable of achieving its administration purpose. Specifically, the blood concentration thereof is not lower than an effective blood concentration of the active form and not higher than a blood concentration at which a side effect is exhibited. For example, it is preferably from about 0.1 pg/mL to about 7 pg/mL, more preferably from about 0.5 pg/mL to about 4 pg/mL. The blood concentration of the active form can be adjusted by a concentration of the compound represented by formula (I) in the adhesive layer, an applied area thereof, a thickness of the adhesive layer or the like.

The amount of the compound represented by formula (I) to be blended in the adhesive preparation of the present invention varies depending on the administration period of time, a blending ratio thereof with the silicone adhesive or the like, however, it is not particularly limited as long as it falls within a range capable of achieving the blood concentration of the active form of the compound of from about 0.1 pg/mL to about 7 pg/mL when it is percutaneously administered. For example, the compound represented by formula (I) is blended in an amount of from about 5 μg/cm² to about 500 μg/cm², preferably from about 10 μg/cm² to about 500 μg/cm², more preferably from about 10 μg/cm² to about 200 μg/cm².

The compound represented by formula (I) may be blended as any one of a dissolving type, a non-dissolving type or a mixed type of the dissolving type and the non-dissolving type. The type is not particularly limited as long as it can maintain its stability; the compound represented by formula (I) is efficiently and continuously permeated in skin; and it can be converted into the active form. Specifically, the dissolving type or the non-dissolving type compound represented by formula (I) alone is blended or the mixed type compound represented by formula (I) of the dissolving type and the non-dissolving type is blended.

In the present invention, the dissolving-type compound represented by formula (I) means that the compound represented by formula (I) exists in the adhesive layer in a completely dissolved state, specifically, it means that crystals of the compound represented by formula (I) are not observed in the adhesive layer by naked eyes or with a light microscope and the adhesive layer is uniform. Further, the drug does not deposit even if it is of a high concentration, and therefore, it has an advantage in that the drug can be retained in the adhesive layer in a completely dissolved state.

In the present invention, the mixed type compound represented by formula (I) of the dissolving type and the non-dissolving type means that the compounds represented by formula (I) in a dissolved state and a non-dissolved state, specifically, in a dissolved state and in a crystalline state or a non-dissolved state are mixed in the adhesive layer. As if compensating for a decrease in the compound represented by formula (I) in the adhesive layer due to the prompt absorption of the dissolving type compound, redissolution of the non-dissolving type compound represented by formula (I) promptly occurs, and thus, because of the absorption of the dissolved compound represented by formula (I), the sustainability of the drug effect can be maintained. A ratio of an elimination rate of the non-dissolving type compound represented by formula (I) to an elimination rate of all types of the compounds represented by formula (I) in the adhesive layer is preferably about 0.1 or higher. In the case where the elimination rate ratio is low, the redissolution of the non-dissolving type drug compensating for the decrease in the dissolving type drug is insufficient, therefore, the sustainability of the drug effect is poor.

As the silicone adhesive to be used in the present invention, [1] a mixture of a component (1): a linear or branched polydimethylsiloxane having a silanol (Si—OH) group at a molecular chain end or in a side chain (hereinafter abbreviated as component (1)) and a component (2): a polysilicate resin having a silanol (Si—OH) group in the molecule (hereinafter abbreviated as component (2)); [2] a condensation reaction product of the component (1) and the component (2); or [3] a mixture of the mixture of the component (1) and the component (2) and the condensation reaction product of the component (1) and the component (2), that is, a mixture of the mixture [1] and the condensation reaction product [2] can be exemplified.

The component (1) is a linear or branched polydimethylsiloxane having a silanol (Si—OH) group at a molecular chain end or in a side chain. As the component (1), a linear polydimethylsiloxane terminated at each of the molecular chain ends with a silanol group and having a viscosity at 25° C. of from 10 to 100,000 mPa·s is preferable, and one having a viscosity at 25° C. of from 1,000 to 50,000 mPa·s can be more preferably used.

The component (2) is a polysilicate resin having a silanol (Si—OH) group in the molecule. More specific examples include a polysilicate resin constituted by structural units M ($R_3SiO_{1/2}$ unit) and Q ($SiO_{4/2}$ unit) in which the substituents R's each independently represent a monovalent organic group or a silanol group, with the proviso that the polysilicate resin has at least one silanol group as a whole. In the present invention, an MQ type polysilicate resin having two or more silanol groups in the molecule can be most preferably used, and it is particularly preferable that the substituents R's are selected from a silanol group, an alkyl group having 1 to 6 carbon atoms and a phenyl group. Further, it may has a structure with an alkoxy group having 1 to 6 carbon atoms in which a part of the silanol group is terminated by an alkyl group having 1 to 6 carbon atoms. A weight average molecular weight of the polysilicate resin in terms of styrene is preferably from 500 to 100,000, more preferably from 1,000 to 15,000. Further, the ratio of M unit to Q unit in the polysilicate resin is preferably from 0.6 to 0.9.

As the silicone adhesive to be used in the present invention, the above-mentioned mixture of the component (1) and the component (2) may be used, however, from the viewpoint of adhesive strength of the silicone adhesive, a condensation reaction product obtained by condensation of both components through a method as described in, for example, Canadian Patent No. 711756 may be used. In the condensation reaction, the polydimethylsiloxane having a silanol group as the component (1) and the polysilicate resin having a silanol group in the molecule as the component (2) are mixed in the absence of a catalyst or in the presence of a catalytic amount of a silanol condensation catalyst and condensed at room temperature or by heating under reflux for 1 to 20 hours. Examples of the silanol condensation catalyst include primary amines, secondary amines, tertiary amines, carboxylic acids of these amines and quaternary ammonium salts. Particularly, ammonia can be preferably used.

The silicone adhesive to be used in the present invention may be improved with regard to storage stability during aging and resistance to an amino functional drug by treating the above-mentioned condensation reaction product of the component (1) and the component (2) with a trimethylsilylating agent such as hexamethylsilazane. Such a silicone adhesive can be obtained by a method described in, for example, JP-A-61-108681 or JP-A-61-158920.

The adhesive strength of the silicone adhesive to be used in the present invention can be adjusted by the molecular weights of the polydimethylsiloxane having a silanol group as the component (1) and the polysilicate resin having a silanol group in the molecule as the component (2) or the blending ratio thereof. The condensation reaction product obtained by selecting desired molecular weight and blending ratio of the respective components and condensing them through a known method, for example, the above-mentioned method can be used. In general, the ratio of the component (1) is in a range of from about 30 to 70 parts by mass.

The silicone adhesive can be used after diluting it with an aromatic hydrocarbon organic solvent (e.g., benzene, toluene, xylene or the like), an aliphatic hydrocarbon organic solvent (e.g., pentane, hexane, heptane or the like), an ester organic solvent (e.g., ethyl acetate, butyl acetate, or the like), or a mixed solvent thereof. Among these solvents, heptane, xylene, ethyl acetate, a mixed solvent thereof or the like is particularly preferable. It is preferable that the silicone adhesive diluted by adding any of the above-mentioned organic solvents in an amount of from 50 to 1000 parts by mass based on 100 parts by mass of the silicone adhesive is used. The viscosity thereof is preferably from 1,000 to 10,000 mPa·s from the viewpoint of coating property, however, it is not limited to this range.

The silicone adhesive to be used in the present invention is an adhesive which forms a bond without the need for addition of a plasticizer and adheres to an adherend when a light pressure is applied. That is why it is called a silicone pressure-sensitive adhesive formulation (PSA). A mixture of the above-mentioned silicone adhesive and the above-mentioned organic solvent is spread on a backing layer and the organic solvent is removed by drying, whereby a pressure-sensitive adhesive layer comprising the silicone adhesive can be formed on the backing layer. Specific examples of such a mixture of the silicone adhesive and the organic solvent include BIO-PSA 7-4601 (trade name), BIO-PSA 7-4501 (trade name), BIO-PSA 7-4401 (trade name), BIO-PSA 7-4602 (trade name), BIO-PSA 7-4502 (trade name), BIO-PSA 7-4402 (trade name), BIO-PSA 7-4301 (trade name), BIO-PSA 7-4201 (trade name), BIO-PSA 7-4101 (trade name), BIO-PSA 7-4302 (trade name), BIO-PSA 7-4202 (trade name) and BIO-PSA 7-4102 (trade name) manufactured by Dow Corning Corporation. These can be used alone or by combining two or more of them. Among these, from the viewpoint of coating property, BIO-PSA 7-4601 (trade name), BIO-PSA 7-4501 (trade name), BIO-PSA 7-4401 (trade name), BIO-PSA 7-4602 (trade name), BIO-PSA 7-4502 (trade name) and BIO-PSA 7-4402 (trade name) are preferable.

In the adhesive preparation of the present invention, the amount of the compound represented by formula (I) is preferably from about 0.01% by mass to about 10% by mass, more preferably from about 0.1% by mass to about 5% by mass, particularly preferably from about 0.1% by mass to about 2% by mass of the total of the adhesive layer.

The adhesive preparation of the present invention can provide controlled drug release and releases the compound represented by formula (I) in a sustained manner without providing rapid release of the compound. In the present invention, this is defined as "sustained release". As also described in Example 3 mentioned below, in a drug release test by the paddle over disk method, the adhesive preparation of the present invention showed a stable release profile in which it showed almost no initial drug release and released about 40% of the drug in 24 hours. Further, in the light of the results of in vitro human skin permeation test, the sustained release adhesive preparation of the present invention can release the drug in a sustained manner for up to about 7 days. Since the sustained release adhesive preparation of the present invention does not provide rapid release of the compound represented by formula (I), it is possible to prevent a rapid increase in the blood concentration of the active form and to avoid an influence on the cardiovascular system such as hypotension or an increase in heart rate or a side effect such as diarrhea. Further, since the preparation releases the compound represented by formula (I) in a sustained manner, the drug effect is sustained.

The adhesive preparation of the present invention is a preparation capable of preventing degradation of the compound represented by formula (I) which is a chemically unstable PG derivative and being stably stored. The term "stability (stable or stably)" as used herein refers to stability (stable or stably) over time, and the adhesive preparation of the present invention can be stored for a long period of time at room temperature. The stability of the adhesive preparation of the present invention can be evaluated using a commonly used stability test (an accelerated test, a stress test or the like). For example, a residual ratio of the compound represented by formula (I-1) after the adhesive preparation of the present invention containing the compound represented by formula (I-1) is stored at 40° C. for 1 month is about 90% or more, preferably 95% or more.

The amount of the compound represented by formula (I) and a degradation product can be measured using a known analysis method (e.g., high performance liquid chromatography, gas chromatography, thin-layer chromatography or the like). In particular, the amount is preferably measured using high performance liquid chromatography. Specifically, for example, the compound represented by formula (I), a degradation product and the like are determined under the test conditions for high performance liquid chromatography (hereinafter abbreviated as HPLC) as described in Example 4 mentioned below, and a ratio of these can be calculated.

The method of stabilizing the compound represented by formula (I) in the adhesive preparation of the present invention is a method of preventing degradation of the chemically unstable compound represented by formula (I). For example, it is a method of maintaining a residual ratio of the compound represented by formula (I) after the adhesive preparation containing the compound represented by formula (I) is stored at 40° C. for 1 month to be about 90% or more, preferably about 95% or more. In order to stabilize the compound represented by formula (I) in the adhesive preparation, the adhesive layer may be constituted only by two components, the compound represented by formula (I) and a silicone adhesive. As the silicone adhesive, the above-mentioned [1] mixture of the component (1) and the component (2); [2] condensation reaction product of the component (1) and the component (2); or [3] mixture of the mixture [1] and the condensation reaction product [2] is preferable. Further, a silicone adhesive in which the viscosity of the component (1) at 25° C. is from 10 mPa·s to 100000 mPa·s and a weight average molecular weight of the component (2) in terms of styrene is from 500 to 100000 is preferable. As also described in Example 4 mentioned below, in the case where the adhesive preparation comprising the adhesive layer constituted by the compound represented by formula (I-1) and the silicone adhesive was stored at 40° C. for 1 month, the content of the compound represented by formula (I-1) did not practically decrease. On the other hand, in the case where the adhesive preparation comprising the adhesive layer constituted by the compound represented by formula (I-1) and an adhesive other than the silicone adhesive was stored at 40° C. for 1 month, the content of the compound represented by formula (I-1) decreased by 10% or more.

In order to administer the adhesive preparation safely, an adhesive preparation showing a small variation in drug skin permeability due to difference in application site, individual difference, the presence or absence of skin lesion such as injury or skin inflammation, etc., that is, an adhesive preparation showing a small change in skin permeability is preferable. The variation in drug skin permeability can be represented by, for example, a ratio between a drug skin permeation rate in the case where the adhesive preparation is applied to a stratum corneum-removed skin which is in a state that the drug permeability is extremely high and a drug skin permeation rate in the case where the adhesive preparation is applied to a skin from which the stratum corneum is not removed (normal skin), that is, a skin permeation rate ratio represented by the following formula.

$$(\text{skin permeation rate ratio}) = (\text{drug skin permeation rate for stratum corneum-removed skin})/(\text{drug skin permeation rate for normal skin}) \quad [\text{Equation 1}]$$

As the skin permeation rate ratio is smaller, a change in skin permeability is smaller. In order to use the adhesive preparation safely, an adhesive preparation having a skin permeation rate ratio of from about 1 to about 5 is preferable. When an adhesive preparation having a high skin permeation rate ratio is used, the drug concentration in the body becomes unstable due to individual difference or difference in application site. When the skin permeation rate is high, there is a risk that the action is too strong or a side effect is caused. If the skin permeation rate ratio falls within a range of from about 1 to about 5, an excellent adhesive preparation can be designed from such a viewpoint.

The method of reducing a change in skin permeability of the compound represented by formula (I) in the adhesive preparation of the present invention is a method of reducing a variation in drug skin permeability due to difference in application site, individual difference, the presence or absence of skin lesion such as injury or skin inflammation, etc., and it is for example, a method of making the above-mentioned skin permeation rate ratio fall within a range of from about 1 to about 5. In order to reduce a change in the skin permeability of the compound represented by formula (I) in the adhesive preparation, the adhesive layer therein may be constituted only by two components, the compound represented by formula (I) and a silicone adhesive. As the silicone adhesive, the above-mentioned [1] mixture of the component (1) and the component (2); [2] condensation reaction product of the component (1) and the component (2); or [3] mixture of the mixture [1] and the condensation reaction product [2] is preferable, further, a silicone adhesive in which the viscosity of the component (1) at 25° C. is from 10 mPa·s to 100000 mPa·s and a weight average molecular weight of the component (2) in terms of styrene is from 500 to 100000 is preferable. As also described in Example 2 mentioned below, in the case where the adhesive preparation comprising the adhesive layer constituted by the compound represented by formula (I-1) and the silicone adhesive was applied to a normal skin and a stratum corneum-removed skin which is in a state that the drug permeability is extremely high, the skin permeation rate did not practically change. On the other hand, when the adhesive preparation comprising the adhesive layer constituted by the compound represented by formula (I-1) and an adhesive other than the silicone adhesive was used, the skin permeation rate in the case where it was applied to a stratum corneum-removed skin significantly increased as compared with the case where it was applied to a normal skin.

In general, examples of the adhesive preparation include a matrix (adhesive single layer) type and a reservoir type, and as the adhesive preparation of the present invention, a matrix type is preferable. Further, in the matrix type, a drug dispersion type, a drug dissolution type and the like are included. The matrix type adhesive preparation is constituted by a structural body comprising an "adhesive layer" having adhesiveness which is formed by combining the compound represented by formula (I) and the silicone adhesive, a "backing layer" and a "liner" which protects the adhesive layer. In the adhesive layer of the drug dispersion type matrix type adhesive preparation, the non-dissolving type compound represented by formula (I) or the mixed type compound represented by formula (I) of the dissolving type and the non-dissolving type is contained, and in the adhesive layer of the drug dissolution type matrix type adhesive preparation, the dissolving type compound represented by formula (I) is contained.

In order to withstand long-term application to the skin and prevent adhesive from remaining on the skin surface at the time of removal by peeling, the thickness of the adhesive layer is preferably from about 20 μm to about 150 μm, more preferably from about 20 μm to about 120 μm, further more preferably from about 20 μm to about 80 μm.

As for the adhesive strength of the adhesive preparation of the present invention, in a ball tack test in accordance with the guidelines in Drug Approval And Licensing Procedures in Japan, in terms of Ball No. of a steel ball which can stop on an adhesive surface for 30 seconds or more, Ball No. 4 or larger is preferable, and Ball No. 7 or larger is more preferable.

The backing layer which constitutes the structural body of the matrix type adhesive preparation of the present invention is not particularly limited, however, it is preferably a backing layer having a flexibility to such an extent that significant discomfort is not caused when it is applied to a skin surface. For example, a single layer film composed of a plastic film (e.g., polyethylene, polyethylene terephthalate, polyurethane, polyethylene, ethylene vinyl acetate, polypropylene, polyester, polyvinyl acetate, ethylene-vinyl acetate copolymer or the like), a metal foil (e.g., aluminum foil or the like), a non-woven cloth, a cotton cloth, a woven cloth, a knitted fabric, a paper or the like or a laminated film thereof can be used. The liner is not particularly limited as long as it can be easily peeled off when the adhesive preparation of the present invention is used and can maintain the adhesive layer before it is covered with the liner. Specifically, for example, a paper subjected to a treatment with a silicone resin or a fluorocarbon polymer, a plastic film (e.g., polyethylene, polyethylene terephthalate, polyurethane, polyethylene, ethylene vinyl acetate, polypropylene, polyester, polyvinyl acetate, an ethylene-vinyl acetate copolymer or the like) or the like can be used.

In the light of the results of the in vitro human skin permeation test, the adhesive preparation of the present invention can release the drug in a sustained manner for up to about 7 days, therefore, a preferable administration method of the adhesive preparation of the present invention is a method in which the adhesive preparation is changed once a day or once in 2 to 7 days. In consideration that the drug concentration in the preparation decreases and the skin permeation rate decreases when the adhesive preparation is applied continuously, a method in which the adhesive preparation is changed once a day or once in 2 to 4 days in order to sufficiently maintain an effective blood concentration of the active form.

Since the adhesive preparation of the present invention has a small change in skin permeability and shows less variation in drug skin permeability due to difference in application site, individual difference, the presence or absence of skin lesion such as injury or skin inflammation, etc., wherever in the body it is applied, the same drug effect can be obtained and it is not necessarily required to be applied to an affected area. Accordingly, the application site of the adhesive preparation of the present invention is not particularly limited as long as it is a site to which the adhesive preparation can be applied. For example, it can be applied to the back of the ear, a brachial region, an abdominal region, a pectoral region, a lower back region, a gluteal region, a leg region (e.g., an inner aspect of the upper thigh, the calf or the like) or the like.

The area of the adhesive preparation of the present invention is preferably from about 1 $cm^2$ to about 100 $cm^2$, more preferably from 1 $cm^2$ to about 50 $cm^2$. A further more preferable applied area of the adhesive preparation is from about 1 $cm^2$ to about 25 $cm^2$. Further, although it may have any shape, it is preferably square, rectangle, circle, oval or the like.

The adhesive preparation of the present invention can be produced by a general production method shown below. A solution or a dispersion liquid to be used for the adhesive layer is prepared by, for example, (1) a solvent method, (2) a heating method (hot melt method) or (3) a calendar method.

The solvent method is a method in which a mixture of the silicone adhesive with an aromatic hydrocarbon organic solvent (e.g., benzene, toluene, xylene or the like), an aliphatic hydrocarbon organic solvent (e.g., pentane, hexane, heptane or the like), an ester organic solvent (e.g., ethyl acetate, butyl acetate or the like), or a mixed solvent thereof and the compound represented by formula (I) or a mixture of the compound represented by formula (I) with any of the above solvents or a mixed solvent thereof are mixed and the resulting mixture is spread and thereafter the solvent is dried off. Preferably, dying is performed at about 20° C. to about 60° C. for about 30 seconds to about 24 hours.

The heating method is a method in which the compound and the silicone adhesive are dissolved and mixed at a high temperature and the resulting mixture is spread and cooled.

The calendar method is a method in which the compound and a base for external preparations are mixed using a mixer and the resulting mixture is spread using a calendar roller. Further, when they have a relatively low viscosity, the compound and a base for external preparations are mixed using a common mixer and the resulting mixture is spread.

The adhesive preparation can be produced by applying the thus obtained solution or dispersion liquid to be used for the adhesive layer to a liner for protection, followed by drying to form the adhesive layer on the liner, and thereafter, bonding a backing layer to the adhesive layer.

As the production method of the adhesive preparation of the present invention, the solvent method is preferable. Additionally, the production method of the adhesive preparation of the present invention is not limited to the above methods, and they may be produced by other efficient methods.

Toxicity

Since toxicity of the compound represented by formulae (I) and (I-A) is sufficiently low and the adhesive preparation of the present can be used safely as pharmaceutical preparations.

Application to Pharmaceutical Preparations

Since the compound represented by formula (I-A) has EP4 agonist activity, it can be used as the adhesive preparation comprising the compound represented by formula (I), for the purpose of prevention, treatment and/or inhibition of progress of diseases such as immune diseases (e.g., autoimmune diseases (e.g., amyotrophic lateral sclerosis (ALS), multiple sclerosis, Sjogren syndrome, articular rheumatism, systemic lupus erythematosus (SLE) and the like), rejection reaction after organ transplantation and the like), asthma, osteodystrophy, nerve cell death, pulmonary injury, hepatopathy, acute hepatitis, glomerulonephritis, renal insufficiency, hypertension, myocardial ischemia, systemic inflammatory response syndrome, pain due to burn, sepsis, hemophagocytosis syndrome, macrophage activation syndrome, Still disease, Kawasaki disease, burn, systemic granuloma, ulcerative colitis, Crohn disease, hypercytokinemia during dialysis, multiple organ failure, shock, dyssomnia, platelet agglutination, gastrointestinal ulcer (e.g., gastric ulcer, duodenal ulcer and the like), stomatitis, boldness, alopecia, bone disease and the like in mammals (e.g., human and non-human animals such as monkey, sheep, cow, horse, dog, cat, rabbit, rat, mouse and the like). In this connection, examples of the bone disease include (1) bone fracture, bone metastasis of cancer, hypercalcemia, Paget disease, bone defect (alveolar bone defect, mandibule defect, childhood idiopathic bone defect and the like), osteonecrosis, (2) primary osteoporosis (e.g., primary osteoporosis accompanied by aging, primary osteoporosis accompanied by menopause, primary osteoporosis accompanied by oophorectomy, vertebral body fracture and the like), (3) secondary osteoporosis (e.g., glucocorticoid-induced osteoporosis, thyroid function induced osteoporosis, fixation induced osteoporosis, heparin induced osteoporosis, immunosuppression induced osteoporosis, osteoporosis due to renal insufficiency, inflammatory osteoporosis, osteoporosis accompanied by Cushing syndrome, rheumatic osteoporosis and the like) and the like. Furthermore, the adhesive preparation comprising the compound represented by formula (I) can be used, for the purpose of accelerating and healing-accelerating osteogenesis after bone operation (e.g., osteogenesis after bone fracture, osteogenesis after bone transplantation, osteogenesis after artificial joint replacement, osteogenesis after spine fusion, osteogenesis after other bone reconstructive operations and the like). Additionally, it can also be used in bone transplantation substitution therapy and the like.

Among the aforementioned various diseases, bone diseases are the most preferable diseases as application of the active form of the present invention, and bone fracture and vertebral body fracture are particularly preferable. Additionally, it is also preferable to use the adhesive preparation comprising the compound represented by formula (I) with the aim of accelerating and healing-accelerating osteogenesis after bone operation (e.g., osteogenesis after bone fracture, osteogenesis after bone transplantation, osteogenesis after artificial joint replacement, osteogenesis after spine fusion, osteogenesis after other bone reconstructive operations and the like). Particularly, in the case of bone fracture, since an affected area is immobilized in a cast, a drug cannot be applied to the affected area in some cases. However, the adhesive preparation of the present invention shows a small change in skin permeability and is capable of exhibiting the same drug effect wherever in the body it is applied and is not necessarily required to be applied to an affected area, and therefore is preferable.

The adhesive preparation of the present invention may be used concomitantly with other agents such as bisphosphonate preparations, vitamin D preparations, calcium preparations, estrogen preparations, calcitonin preparations, ipriflavone preparations, protein assimilation steroids, vitamin K preparations, cathepsin K inhibitors, parathyroid hormones, growth factors, caspase-1 inhibitors, PTHrP derivatives, metalloproteinase inhibitors, farnesoid X receptor agonists, anti-androgen agents, selective estrogen receptor modulators (SERMs), progesterone agonists, calcium receptor antagonists (calcilytics), strontium preparations, α-calcitonin gene-related peptide preparations, bone morphogenetic protein preparations, anti-RANKL antibodies, anti-TNF-α antibodies, anti-IL-6 antibodies and the like. The agents which are used in combination may be contained in the adhesive preparation of the present invention. Additionally, administration method of the agents which are used in combination is not particularly limited and is either oral administration or parenteral administration.

Examples of the bisphosphonate preparations include alendronate sodium hydrate, ibandronic acid, incadronate disodium, etidronate disodium, olpadronate, clodronate sodium hydrate, zoledronic acid, tiludronate disodium, neridronate, pamidronate disodium, piridronate, minodronic acid hydrate, sodium risedronate hydrate, YM 175 and the like.

Examples of the vitamin D preparations include alfacalcidol, falecalcitriol, calcitriol, 1α, 25-dihydroxycholecalciferol, dihydrotachysterol, ST-630, KDR, ED-71, rocaltrol (Ro 44-7190), tacalciol, maxacalcitol and the like.

Examples of the calcium preparations include calcium chloride, calcium gluconate, calcium glycerophosphate, calcium lactate, calcium L-aspartate, calcium phosphate dibasic and the like.

Examples of the estrogen preparations include estradiol, estradiol benzoate, estradiol cypionate, estradiol dipropionate, estradiol enanthate, estradiol hexahydrobenzoate, estradiol phenylpropionate, estradiol undecanoate, estradiol valerate, estrone, ethynyl estradiol, mestranol and the like.

Examples of the calcitonin preparations include calcitonin, sermon calcitonin (STH-32, SMC 20-51), chicken calcitonin (MCI-536), secalciferol, elcatonin, TJN-135 and the like.

Examples of the ipriflavone preparations include ipriflavone and the like.

Examples of the protein assimilation steroids include oxymetholone, stanozolol, nandrolone decanoate, nandrolone phenylpropionate, nandrolone cyclohexylpropionate, metenolone acetate, mestanolone, ethylestrenol, calusterone and the like.

Examples of the vitamin K preparations include menatetrenone, phytonadione and the like.

Examples of the cathepsin K inhibitors include ONO-5334, AAE 581, SB 462795 and the like.

Examples of the parathyroid hormone (PTH) include dried thyroid, levothyroxine sodium, liothyronine sodium, propylthiouracil, thiamazole, teriparatide acetate and the like.

Examples of the growth factors include fibroblast growth factor (FGF), vascular endothelial growth factor (VEGF), hepatocyte growth factor (HGF), insulin-like growth factor (IGF) and the like.

Examples of the caspase-1 inhibitors include nitroflubiprofen, pralnacasan and the like.

Examples of the PTHrP derivatives include hPTHrP, RS-66271 and the like.

Examples of the farnesoid X receptor agonists include SR-45023A and the like.

Examples of the anti-androgen agents include osateron acetate and the like.

Examples of the selective estrogen receptor modulators (SERMs) include TSE-424, WJ-713/MPA, lasofoxifene tartrate, raloxifene hydrochloride, tamoxifen citrate and the like.

Examples of the progesterone agonists include trimegestone and the like.

Examples of the calcium receptor antagonists (calcilytics) include NPS-423557 and the like.

Examples of the strontium preparations include strontium ranelate and the like.

Examples of the anti-RANKL antibodies include AMG 162 and the like.

Examples of the bone morphogenetic protein preparations include YM 484 and the like.

Examples of the anti-TNF-α antibodies include infliximab, etanercept, adalimumab and the like.

The other agent which is used in combination and described above are examples and not limited thereto.

The other agent may be administered in combination of two or more of optional species. Additionally, not only the substances so far found but also those which will be found in the future based on the aforementioned mechanism are included in the other agent which is used in combination.

Effect of the Invention

Since the adhesive preparation of the present invention comprising an adhesive layer containing two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and a silicone adhesive is capable of releasing the C1-4 alcohol ester in a sustained manner without providing rapid release, the blood concentration does not rapidly increase and side effects can be avoided, and the drug effect can be sustained. Further, since the adhesive preparation of the present invention is stable over time, it can be stored at room temperature for a long period of time. Further, since the adhesive preparation of the present invention shows a small variation in drug skin permeability due to difference in application site, individual difference, the presence or absence of skin lesion such as injury or skin inflammation, etc., it can be applied to any site.

BEST MODE FOR CARRYING OUT THE INVENTION

The following describes the present invention in detail with preparation examples and examples, but the present invention is not limited thereto.

Additionally, the following preparation examples may be changed within the scope which does not depart from the scope of the present invention.

PREPARATION EXAMPLES

Preparation Example 1

Silicone Preparation Containing 0.5% Compound A

A compound represented by formula (I-1) (hereinafter abbreviated as Compound A) was dissolved in ethyl acetate (Kishida Chemical Co., Ltd.), whereby a drug solution (10 mg/mL) was prepared. The thus prepared drug solution (1 mL) was mixed with a silicone adhesive (BIO-PSA 7-4601 (trade name), Dow Corning Corporation) (3316.7 mg), whereby a coating liquid was prepared. The thus prepared coating liquid was spread on a backing layer (Scotchpak #1022 (trade name), 3M Health Care Limited) to a thickness of about 80 μm using an applicator. The adhesive surface was dried at room temperature. The dried adhesive surface was covered with a release liner (Scotchpak #1022 (trade name), 3M Health Care Limited) and cut into a circle of 0.64 cm$^2$ for attaching it to a Franz-type cell (opening area: 0.64 cm$^2$) in Examples 1 and 2 mentioned below, whereby the adhesive preparation of the present invention (Preparation 1 (content of Compound A: 40 μg/cm$^2$)) was obtained.

Preparation example 2

Silicone Preparation Containing 1% Compound A

Compound A (60 mg) was mixed with a silicone adhesive (BIO-PSA 7-4501 (trade name), Dow Corning Corporation) (9740.9 mg), whereby a coating liquid was prepared. The thus prepared coating liquid was spread on a backing layer (Scotchpak #1022 (trade name), 3M Health Care Limited) to a thickness of about 80 μm using an applicator. The adhesive surface was dried at room temperature. The dried adhesive surface was covered with a release liner (Scotchpak #1022 (trade name), 3M Health Care Limited) and cut into a circle of 8 cm$^2$, whereby the adhesive preparation of the present invention (Preparation 2 (content of Compound A: 80 μg/cm$^2$)) was obtained.

Preparation example 3

Silicone Preparation Containing 1% Compound A

Compound A (60 mg) was mixed with a silicone adhesive (BIO-PSA 7-4501 (trade name), Dow Corning Corporation) (9740.9 mg), whereby a coating liquid was prepared. The thus prepared coating liquid was spread on a backing layer (Scotchpak #1022 (trade name), 3M Health Care Limited) to a thickness of about 80 μm using an applicator. The adhesive surface was dried at room temperature. The dried adhesive surface was covered with a release liner (Scotchpak #1022 (trade name), 3M Health Care Limited) and cut into a square of 4 cm$^2$, whereby the adhesive preparation of the present invention (Preparation 3 (content of Compound A: 80 μg/cm$^2$)) was obtained.

Preparation example 4

Silicone Preparation Containing 0.3% Compound A

Compound A was dissolved in ethyl acetate (Kishida Chemical Co., Ltd.), whereby a drug solution (24 mg/mL)

was prepared. The thus prepared drug solution (1 mL) was mixed with a silicone adhesive (BIO-PSA 7-4601 (trade name), Dow Corning Corporation) (13293.3 mg), whereby a coating liquid was prepared. The thus prepared coating liquid was spread on a backing layer (Scotchpak #1022 (trade name), 3M Health Care Limited) to a thickness of about 80 μm using an applicator. The adhesive surface was dried at room temperature. The dried adhesive surface was covered with a release liner (Scotchpak #1022 (trade name), 3M Health Care Limited) and cut into a square of 4 cm$^2$, whereby the adhesive preparation of the present invention (Preparation 4 (content of Compound A: 25 μg/cm$^2$)) was obtained.

Preparation example 5

Silicone Preparation Containing 0.5% Compound A

Compound A was dissolved in ethyl acetate (Kishida Chemical Co., Ltd.), whereby a drug solution (20 mg/mL) was prepared. The thus prepared drug solution (0.5 mL) was mixed with a silicone adhesive (BIO-PSA 7-4401 (trade name), Dow Corning Corporation) (3316.7 mg), whereby a coating liquid was prepared. The thus prepared coating liquid was spread on a backing layer (Scotchpak #1022 (trade name), 3M Health Care Limited) to a thickness of about 80 μm using an applicator. The adhesive surface was dried at room temperature. The dried adhesive surface was covered with a release liner (Scotchpak #1022 (trade name), 3M Health Care Limited) and cut into a square of 6.25 cm$^2$, whereby the adhesive preparation of the present invention (Preparation 5 (content of Compound A: 40 μg/cm$^2$)) was obtained.

Comparative Example 1

SIS Preparation Containing 1% Compound A

A styrene-isoprene-styrene block copolymer (hereinafter abbreviated as SIS, SIS-5229 (trade name), JSR) (577 mg), an ultra-hypochromic rosin ester (KE-311, Arakawa Chemical Industries, Ltd.) (577 mg) and a light liquid paraffin (No. 70-S (trade name), Sanko Chemical Industry Co., Ltd.) (626 mg) were dissolved in ethyl acetate (Kishida Chemical Co., Ltd.) (2000 mg), whereby an adhesive liquid was prepared. Compound A (40 mg) and oleyl alcohol (hereinafter abbreviated as OLA, AO-85S (trade name), NOF Corporation) (200 mg) were dissolved in the thus prepared adhesive liquid, whereby a coating liquid was prepared. The thus prepared coating liquid was spread on a backing layer (Scotchpak #1022 (trade name), 3M Health Care Limited) to a thickness of about 60 μm using an applicator. The adhesive surface was dried at room temperature. The dried adhesive surface was covered with a release liner (Scotchpak #1022 (trade name), 3M Health Care Limited) and cut into a circle of 0.64 cm$^2$, whereby an adhesive preparation as a comparative example (Comparative preparation 1 (content of Compound A: 60 μg/cm$^2$)) was obtained.

Comparative Example 2

SIS Preparation Containing 1% Compound A

SIS (SIS-5229 (trade name), JSR) (577 mg), a rosin ester (KE-311 (trade name), Arakawa Chemical Industries, Ltd.) (577 mg) and a light liquid paraffin (No. 70-S (trade name), Sanko Chemical Industry Co., Ltd.) (626 mg) were dissolved in ethyl acetate (Kishida Chemical Co., Ltd.) (2000 mg), whereby an adhesive liquid was prepared. Compound A (40 mg) and OLA (AO-85S (trade name), NOF Corporation) (200 mg) were dissolved in the thus prepared adhesive liquid, whereby a coating liquid was prepared. The thus prepared coating liquid was spread on a backing layer (Scotchpak #1022 (trade name), 3M Health Care Limited) to a thickness of about 60 μm using an applicator. The adhesive surface was dried at room temperature. The dried adhesive surface was covered with a release liner (Scotchpak #1022 (trade name), 3M Health Care Limited) and cut into a circle of 8 cm$^2$, whereby an adhesive preparation as a comparative example (Comparative preparation 2 (content of Compound A: 60 μg/cm$^2$)) was obtained.

Comparative Example 3

Sis Preparation Containing 2% Compound A

SIS (SIS-5229 (trade name), JSR) (4 g), a high molecular weight polyisobutylene (Vistanex MML-10 (trade name), Exxon Chemical Company) (0.6 g), a low molecular weight polyisobutylene (Oppanol B12SPN (trade name), BASF Japan) (1.4 g), an ester gum (KE-311 (trade name), Arakawa Chemical Industries, Ltd.) (0.8 g), an alicyclic saturated hydrocarbon resin (Alcon P-100 (trade name), Arakawa Chemical Industries, Ltd.) (5.2 g), a liquid paraffin (Hicall M352 (trade name), Kaneda Co., Ltd.) (6.56 g), OLA (AO-85S (trade name), NOF Corporation) (1 g) and di-t-butylhydroxytoluene (Yoshinox (trade name), API Corporation) (0.04 g) were dissolved in n-hexane (20 g), whereby an adhesive liquid was prepared. Compound A (0.04 g) was dissolved in the thus prepared adhesive liquid, whereby a coating liquid was prepared. The thus prepared coating liquid was spread on a backing layer (Scotchpak #1022 (trade name), 3M Health Care Limited) to a thickness of about 60 μm using an applicator. The adhesive surface was dried at room temperature. The dried adhesive surface was covered with a release liner and cut into a square of about 4 cm$^2$, whereby an adhesive preparation as a comparative example (Comparative preparation 3 (content of Compound A: 200 μg/cm$^2$)) was obtained.

EXAMPLES

Example 1

In Vitro Human Skin Permeability Test

A human skin (a dorsal or a femoral skin: a man of 72 years old (n=2), a man of 63 years old, a man of 74 years old, and a man of 78 years old) obtained from Hans Biomed Corp. was attached to a Franz-type cell (opening area: 0.64 cm$^2$) and Preparation 1 was applied to the stratum corneum side. To the dermis side cell, physiological saline (4 mL) was applied. A 0.5 mL portion was collected over a time course from the dermis layer side cell and Compound A and its active form, 4-{[2-((1R,2R,3R)-3-hydroxy-2-{(1E,3S)-3-hydroxy-4-[3-(methoxymethyl)phenyl]but-1-enyl}-5-oxocyclopentyl) ethyl]sulfanyl} butanoic acid (hereinafter abbreviated as Compound B) were determined by the LC/MS/MS method under the conditions shown below. The total cumulative permeation amount up to 48 hours was calculated, and the skin permeation rate was calculated from the slope.

<Determination in Skin Permeability Test (LC/MS/MS)>

20 μL of a receptor solution was placed in a microtube, 180 μL of acetonitrile was added thereto and mixed well, and the resulting mixture was centrifuged (12000 rpm, 5 min). 50 μL of the supernatant was placed in a glass test tube, 150 μL of a mixed liquid of 0.1% acetic acid and acetonitrile (20:80) was added thereto and mixed well, and the resulting mixture was used as an injection sample.

<Measurement Conditions>

(1) Measurement of Compound A (1-1) LC conditions

Column: YMC-Pak MB-ODS 2.0×50 mm, 3 μm (YMC)

Column temperature: room temperature

Gradient:

TABLE 1

| Total Time | 0.1% acetic acid | CH₃CN |
|---|---|---|
| 0.00 min | 80% | 20% |
| 3.00 min | 20% | 80% |
| 6.00 min | 20% | 80% |
| 6.01 min | 80% | 20% |
| 10.00 min | 80% | 20% |

Flow rate: 0.2 mL/min
Autosampler temperature: 10° C.
Measurement time: 10 min
Amount of injection: 10 μL
(1-2) MS/MS conditions

TABLE 2

| Ion Source | Electrospray ionization |
|---|---|
| Ion detection mode | Positive Ion |
| Monitor Ion 433.2 | Precursor Ion (m/z) Product Ion (m/z) 101.1 |

TABLE 2-continued

| DP | 86 V |
|---|---|
| EP | 10 V |
| CE | 25 V |
| CXP | 8 V |
| Collision Gas | 5 |
| Curtain Gas | 10 psi |
| Ion Source Gas 1 | 30 psi |
| Ion Source Gas 2 | 50 psi |
| Ion Spray Voltage | 5500 V |
| Temperature | 700° C. |

(2) Measurement of Compound B
(2-1) LC conditions
Column: YMC-Pak MB-ODS 2.0×50 mm, 3 μm (YMC)
Column temperature: room temperature
Gradient:

TABLE 3

| Total Time | 0.1% acetic acid | CH₃CN |
|---|---|---|
| 0.00 min | 80% | 20% |
| 3.00 min | 20% | 80% |
| 5.00 min | 20% | 80% |
| 5.01 min | 80% | 20% |
| 9.00 min | 80% | 20% |

Flow rate: 0.2 mL/min
Autosampler temperature: 10° C.
Measurement time: 9 min
Amount of injection: 10 μL (2-2) MS/MS conditions

TABLE 4

| Ion Source | Electrospray ionization |
|---|---|
| Ion detection mode | Negative Ion |
| Monitor Ion 435.2 | Precursor Ion (m/z) Product Ion (m/z) 119 |
| DP | −55 V |
| EP | −10 V |
| CE | −24 V |
| CXP | −9 V |
| Collision Gas | 5 |
| Curtain Gas | 40 psi |
| Ion Source Gas 1 | 30 psi |
| Ion Source Gas 2 | 30 psi |
| Ion Spray Voltage | −4500 V |
| Temperature | 600° C. |

<Results>

Figure 1:
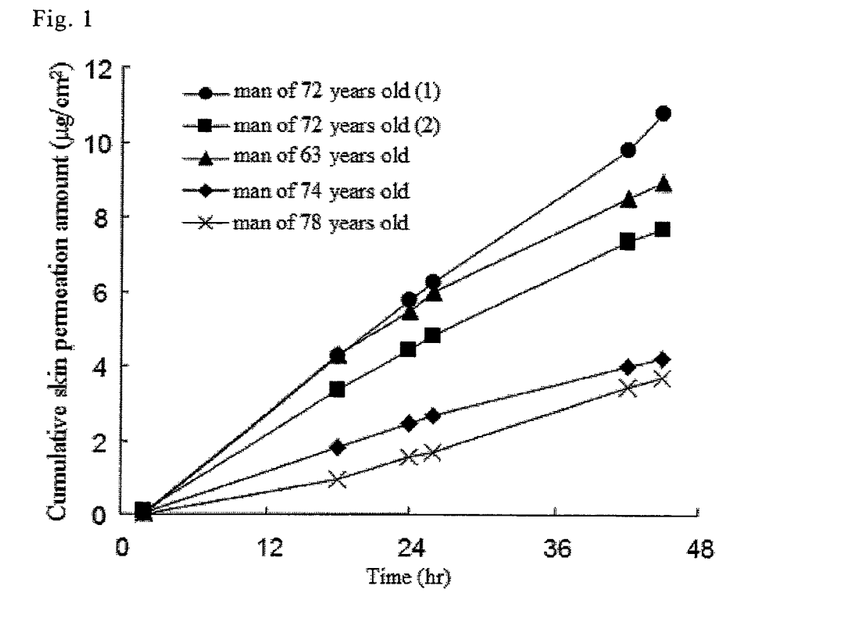
FIG. 1 shows results of an in vitro human skin permeability test for Preparation 1.

The results obtained in the above-mentioned in vitro human skin permeability test are shown in FIG. 1.

Further, the respective human skin permeation rates were calculated from the slopes of this human skin permeation profile.

TABLE 5

| | Sample Used skin (YM = years old man) | | | | | |
|---|---|---|---|---|---|---|
| | 63 YM | 74 YM | 78 YM | 72' YM | 72 YM | Average |
| Human skin permeation rate (μg/cm²/h) | 0.173 | 0.089 | 0.105 | 0.260 | 0.199 | 0.165 |
| Applied skin area (cm²) | 2.6 | 2.6 | 2.6 | 2.6 | 2.6 | 2.6 |
| Systemic clearance (L/hr) | 310.8 | 310.8 | 310.8 | 310.8 | 310.8 | 310.8 |
| Estimated blood concentration (pg/mL) | 1.5 | 0.7 | 0.9 | 2.2 | 1.7 | 1.4 |

When a steady-state blood concentration was estimated by dividing the human skin permeation rate by the systemic clearance from Table 5, it was suggested that a blood concentration of about 1.4 pg/mL from which a sufficient drug effect is predicted to be obtained is obtained with the applied area of about 2.6 cm².

Example 2

In Vitro Permeability Test Using Human Stratum Corneum-Removed Skin

Figure 2:
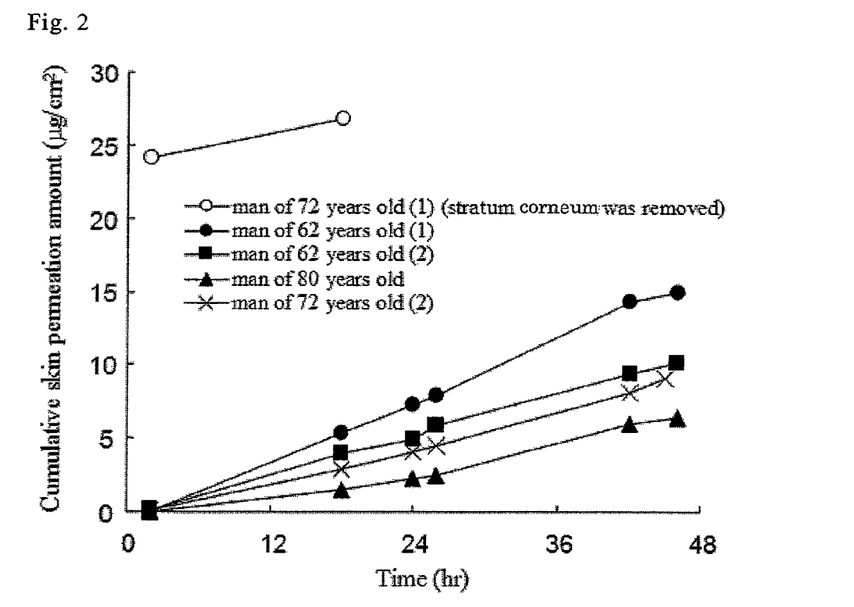
FIG. 2 shows results of an in vitro permeability test for Comparative preparation 1 using human stratum corneum-removed skin.
Figure 3:
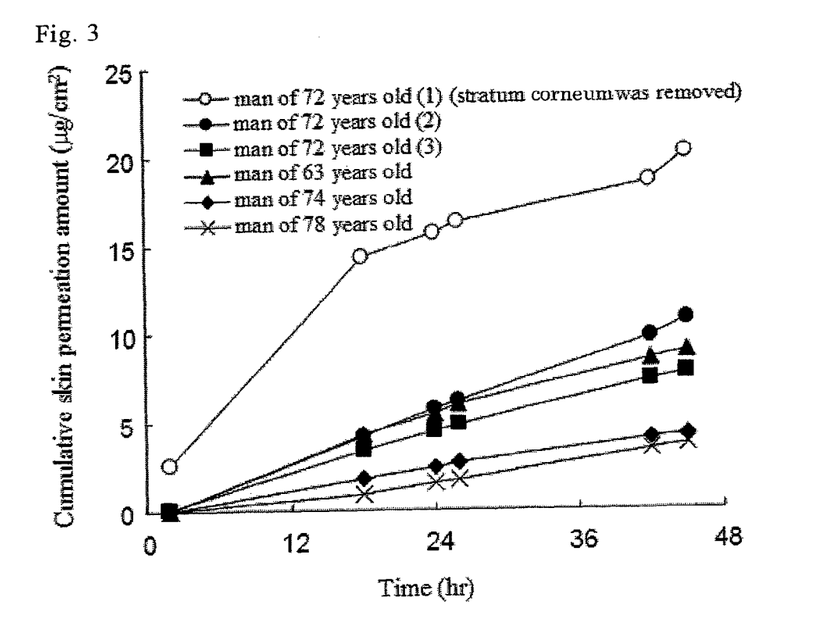
FIG. 3 shows results of an in vitro permeability test for Preparation 1 using human stratum corneum-removed skin.

A procedure in which tape was adhered to and removed from a human skin (a dorsal or a femoral skin: a man of 72 years old (n=2), a man of 62 years old (n=2) and a man of 80 years old (these were used in the test for Comparative preparation 1); a man of 72 years old (n=3), a man of 63 years old, a man of 74 years old, and a man of 78 years old (these were used in the test for Preparation 1)) obtained from Hans Biomed Corp. on the stratum corneum side was repeated 20 times, whereby a stratum corneum-removed skin was prepared. The stratum corneum-removed skin was attached to a Franz-type cell (opening area: 0.64 cm²) and Preparation 1 or Comparative preparation 1 was applied to the epidermis side. To the dermis side cell, physiological saline (4 mL) was applied. A 0.5 mL portion was collected over a time course from the dermis layer side cell and Compound A and its active form, Compound B were determined by the LC/MS/MS method under the same conditions as in Example 1. The obtained results are shown in FIG. 2 and FIG. 3. The total cumulative permeation amount up to 48 hours was calculated, and the skin permeation rate was calculated from the slope.

TABLE 6

| Preparation | Permeation rate ratio stratum corneum-removed skin/normal skin |
|---|---|
| Comparative preparation 1 | 41.4 |
| Preparation 1 | 3.3 |

<Results>

When evaluation of permeability in the stratum corneum-removed skin was performed, in the case of Comparative preparation 1, prompt skin permeation was observed and the permeation rate increased by about 40 times as compared with the normal skin from which the stratum corneum was not removed. On the other hand, in the case of Preparation 1 which is the adhesive preparation of the present invention, even in the stratum corneum-removed skin, an increase in the permeation rate was significantly prevented and the permeation rate increased by only about 3 times or so as compared with the normal skin. The adhesive preparation of the present invention comprising a combination of Compound A and the silicone adhesive showed little change in the permeation rate even in the stratum corneum-removed skin which is in a state that the drug permeability is extremely high, therefore, a change in skin permeability depending on the application site or the like could be reduced.

Example 3

Drug Release Test

The drug release was evaluated by the paddle over disk method. Preparation 2 or Comparative preparation 2 was fixed on a disk, and a drug release test was performed under the following conditions.
<Dissolution Test Conditions>
Dissolution tester: DISSOLUTION TESTER NTR-6100 (Toyama Sangyo Co., Ltd.)
Test liquid: physiological saline (Otsuka Pharmaceutical Factory, Inc.)
Amount of test liquid: 500 mL
Temperature of test liquid: 32+/−0.5° C.
Sampling time: 15, 30, 60, 120, 240, 480, 720, 1440 min
Paddle rotation speed: 50 rpm
Amount of sampling: 5 mL
<Determination Method>
A sampling liquid was injected into HPLC, and Compound A was determined under the following conditions.
<HPLC Conditions>
Detector: ultraviolet absorptiometer (measurement wavelength: 210 nm)
Column: YMC-Pack Pro $C_{18}$ AS-302 (4.6 mm i.d., 150 mm)
Column temperature: 50° C.
Mobile phase: 0.1 M phosphoric acid/acetonitrile mixed liquid (60:40)
Flow rate: 1.0 mL/min
Cooler temperature: 5° C.
Analysis time: 10 min
Amount of injection: Calibration liquid: 20 μL, Sample: 70 μL
<Results>

Figure 4:
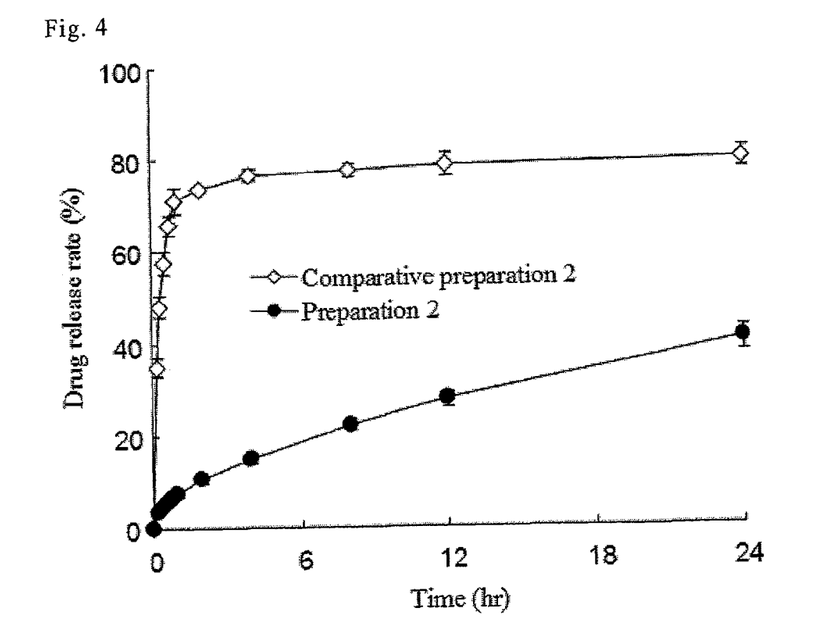
FIG. 4 shows results of a drug release test for Preparation 2 and Comparative preparation 2.

The results of the above-mentioned drug release test are shown in FIG. 4. In the case of Comparative preparation 2 using SIS as the adhesive, prompt drug release was observed.

On the other hand, in the case of Preparation 2 containing the silicone adhesive of the present invention, the drug was released in a sustained manner without providing rapid drug release, and it could be confirmed that drug release from the preparation is controlled.

From the above results, it was suggested that the adhesive preparation of the present invention has an ability to control drug release and is a safe and effective sustained release preparation without providing rapid drug release.

Example 4

Stability Test

Each of Preparation 3, Preparation 4 and Comparative preparation 3 was placed in an aluminum moisture-proof bag. The bag was heat-sealed and subjected to a stability test by placing it under each condition (40° C.: 1, 3, 4 months, 25° C.: 4 months, 5° C.: 4 months).
<Purity Test Method>
The content of Compound A in the preparation subjected to the stability test under each condition and generation of impurities were measured by HPLC.
(1) Purity Test for Comparative Preparation 3
To Comparative preparation 3, hexane (20 mL) was added, and the resulting mixture was shaked for 15 minutes. Then, 10 mL of a mixed liquid of water and acetonitrile (7:3) was added thereto, and the resulting mixture was shaken for an additional 15 minutes. The mixture was centrifuged at 2000 rpm for 5 minutes, and the lower layer was obtained in an amount of 9 mL. Further, to the upper layer, 10 mL of a mixed liquid of water and acetonitrile (7:3) was added again and the resulting mixture was shaken for 15 minutes. Then, the mixture was centrifuged at 2000 rpm for 5 minutes, and the lower layer was obtained in an amount of 9 mL. 18 mL of the lower layer was used as a sample solution and was subjected to the measurement under the following HPLC conditions.
<HPLC Conditions>
Detector: ultraviolet absorptiometer (measurement wavelength: 210 nm)
Column: YMC-Pack Pro $C_{18}$ AS-302 (4.6 mm i.d., 150 mm)
Column temperature: 50° C.
Mobile phase: A: water/methanol mixed liquid (9:1)
B: acetonitrile/methanol mixed liquid (6:4)
The measurement was performed by changing the solvent ratio over the time course according to the following Table 7.

TABLE 7

| Time (min) | Mobile phase A (%) | Mobile phase B (%) |
|---|---|---|
| 0 | 70 | 30 |
| 40 | 45 | 55 |
| 50 | 10 | 90 |
| 50.01 | 70 | 30 |
| 60 | 70 | 30 |

Flow rate: 1.0 mL/min
Cooler temperature: 5° C.
Analysis time: 60 min
Amount of injection: 50 μL
(2) Purity Test for Preparation 3
To Preparation 3, acetonitrile (10 mL) was added, and the resulting mixture was subjected to stirring extraction at 500 rpm for 24 hours. Then, 1 mL of the extract liquid was taken out, and water (1 mL) was added thereto and mixed therewith. The resulting mixture was filtered through a 0.2 μm filter, and the filtrate was used as a sample solution and was subjected to measurement under the following HPLC conditions.
<HPLC Conditions>
Detector: ultraviolet absorptiometer (measurement wavelength: 210 nm)
Column: YMC-Pack Pro $C_{18}$ AS-302 (4.6 mm i.d., 150 mm)
Column temperature: 60° C.
Mobile phase: A: water/methanol mixed liquid (9:1)
B: acetonitrile/methanol mixed liquid (6:4)

The measurement was performed by changing the solvent ratio over the time course according to the following Table 8.

TABLE 8

| Time (min) | Mobile phase A (%) | Mobile phase B (%) |
|---|---|---|
| 0 | 70 | 30 |
| 40 | 45 | 55 |
| 50 | 10 | 90 |
| 50.01 | 70 | 30 |
| 60 | 70 | 30 |

TABLE 9

| Time (min) | Mobile phase A (%) | Mobile phase B (%) |
|---|---|---|
| 0 | 70 | 30 |
| 40 | 45 | 55 |
| 50 | 10 | 90 |
| 50.01 | 70 | 30 |
| 60 | 70 | 30 |

Flow rate: 1.0 mL/min
Cooler temperature: 5° C.
Analysis time: 60 min
Amount of injection: 100 μL
<Results>

The results of the above-mentioned stability test are shown in the following Table 10.

TABLE 10

| Preparation | Test conditions | Area % | | | |
|---|---|---|---|---|---|
| | | Compound A | Degradation product 1 | Degradation product 2 | Others |
| Comparative Preparation 3 | Initial | 95.7 | 0.2 | 0.2 | 3.9 |
| | 40° C.-1 M | 85.8 | 5.1 | 3.9 | 5.2 |
| Preparation 3 | Initial | 97.8 | 0.7 | 0 | 1.5 |
| | 40° C.-1 M | 97.5 | 0.8 | 0.4 | 1.2 |
| | 40° C.-3 M | 96.5 | 0.7 | 1.2 | 1.6 |
| Preparation 4 | 5° C.-4 M | 97 | 0 | 1.5 | 1.6 |
| | 25° C.-4 M | 96.8 | 0 | 1.6 | 1.5 |
| | 40° C.-4 M | 94.8 | 0.3 | 3.1 | 1.8 |

Flow rate: 1.0 mL/min
Cooler temperature: 5° C.
Analysis time: 60 min
Amount of injection: 100 μL (3) Purity Test for Preparation 4

To Preparation 4, hexane (20 mL) was added, and the resulting mixture was shaken for 15 minutes. Then, 1 mL of an internal standard solution (methyl 4-hydroxybenzoate) (120.02 μg/mL) and 1 mL of an acetonitrile solution were added thereto, and further 8 mL of a mixed liquid of 0.1 M phosphoric acid and acetonitrile (1:7) was added thereto, and the resulting mixture was shaken for 15 minutes. The mixture was centrifuged at 2000 rpm for 5 minutes and the lower layer was obtained in an amount of 2 mL. To 2 mL of this lower layer, water (2 mL) was added and mixed therewith, and the resulting mixture was centrifuged at 2000 rpm for 5 minutes to obtain the lower layer. The thus obtained lower layer was used as a sample solution and was subjected to measurement under the following HPLC conditions.
<HPLC Conditions>
Detector: ultraviolet absorptiometer (measurement wavelength: 210 nm)
Column: YMC-Pack Pro $C_{18}$ AS-302 (4.6 mm i.d., 150 mm)
Column temperature: 60° C.
Mobile phase: A: water/methanol mixed liquid (9:1)
B: acetonitrile/methanol mixed liquid (6:4)

The measurement was performed by changing the solvent ratio over the time course according to the following Table 9.

In the case of Comparative preparation 3, the content of Compound A after storage at 40° C. for 1 month decreased by 10% or more. On the other hand, in the case of Preparation 3 and Preparation 4, a significant decrease in the drug content was not observed even after storage at 40° C. for 4 months.

From the above results, it was suggested that the adhesive preparation of the present invention is stable over time and can be stored at room temperature for a long period of time.

Example 5

Rabbit Skin Irritation Test

Preparation 5 was percutaneously administered to a dorsal region of a Japanese white male rabbit in an occlusive manner for 24 hours. The skin reactions at 24 hours after administration (about 30 minutes after removal of occlusion) and at 48 hours after administration were observed and evaluated in accordance with the evaluation criteria of Draise "The Journal of Pharmacology and Experimental Therapeutics, vol. 83, pp. 377-390, 1944" shown in the table (Table 11).

TABLE 11

| | Grade |
|---|---|
| A. Erythema and crust | |
| No erythema | 0 |
| Very slight erythema (barely perceptible) | 1 |
| Well defined erythema | 2 |

TABLE 11-continued

|  | Grade |
|---|---|
| Moderate to severe erythema | 3 |
| Severe erythema of beet redness with slight crust formation (injuries in deep region) | 4 |
| B. Edema | |
| No edema | 0 |
| Very slight edema (barely perceptible) | 1 |
| Well defined edema (clearly distinguishable from the periphery) | 2 |
| Moderate to severe edema (raised about 1 mm) | 3 |
| Severe edema (raised 1 mm or more and extending to the periphery) | 4 |

A primary irritation index (PII) was calculated from an average grade of each animal at the time of removal of the test sample (24 hours after administration) and at the time of 24 hours after the removal (48 hours after administration). PII=Total of average grade of each sample/3

The safety classification is as follows: (i) a substance has no irritation when PII is 0, (ii) a substance is a mild irritant when PII exceeds 0 and is 2 or less, (iii) a substance is a moderate irritant when PII exceeds 2 and is 5 or less, and (iv) a substance is a severe irritant when PII exceeds 5.
<Results>
PII of Preparation 5 was 1.50. Therefore, it was suggested that the adhesive preparation of the present invention is a safe preparation with less skin irritation.

INDUSTRIAL APPLICABILITY

The adhesive preparation of the present invention can be stored at room temperature for a long period of time and can also avoid side effects, therefore, it can be used as a safe pharmaceutical preparation.

The invention claimed is:

1. A sustained release adhesive preparation which is stable and has a low skin permeation rate ratio, comprising a sustained release adhesive layer containing two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and a silicone adhesive.

2. The preparation according to claim 1, wherein a concentration of the C1-4 alcohol ester is from 0.1% by mass to 5% by mass of the total of the adhesive layer.

3. The preparation according to claim 1, wherein a concentration of the C1-4 alcohol ester is from 10 μg/cm² to 500 μg/cm².

4. The preparation according to claim 1, wherein an area of the adhesive preparation is from 1 cm² to 100 cm².

5. The preparation according to claim 1, wherein a thickness of the adhesive layer is from 20 μm to 150 μm.

6. The preparation according to claim 1, wherein the C1-4 alcohol ester is methyl 4-{[2((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate.

7. The preparation according to claim 1, wherein a residual ratio of the C1-4 alcohol ester after storage at 40° C. for 1 month is 90% or more.

8. The preparation according to claim 1, wherein a skin permeation rate ratio for a stratum corneum-removed skin to that for a normal skin is from 1 to 5.

9. The preparation according to claim 1, wherein the silicone adhesive is:
   [1] a mixture of a component (1): a linear or branched polydimethylsiloxane having a silanol group at a molecular chain end or in a side chain and a component (2): a polysilicate resin having a silanol group in the molecule;
   [2] a condensation reaction product of the component (1) and the component (2); or
   [3] a mixture of the mixture [1] and the condensation reaction product [2].

10. The preparation according to claim 9, wherein a viscosity of the component (1) at 25° C. is from 10 mPa·s to 100000 mPa·s and a weight average molecular weight of the component (2) in terms of styrene is from 500 to 100000.

11. The preparation according to claim 1, wherein the adhesive layer is produced by mixing a solution having a viscosity of from 1000 mPa·s to 10000 mPa·s obtained by adding 50 to 1000 parts by mass of an aromatic hydrocarbon organic solvent, an aliphatic hydrocarbon organic solvent, an ester organic solvent, or a mixed solvent thereof to 100 parts by mass of the silicone adhesive with the C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid as such or a mixture thereof with an aromatic hydrocarbon organic solvent, an aliphatic hydrocarbon organic solvent, an ester organic solvent, or a mixed solvent thereof.

12. The preparation according to claim 1 which is for the prevention, treatment and/or inhibition of progression of a bone disease.

13. The preparation according to claim 12, wherein the bone disease is bone fracture.

14. A sustained release adhesive preparation which is stable and has a low skin permeation rate ratio, comprising a sustained release adhesive layer containing two components, methyl 4-{[2((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate and a silicone adhesive and satisfying the following conditions (1) to (6):
   (1) a concentration of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate is from 0.1% by mass to 2% by mass of the total of the adhesive layer;
   (2) a concentration of methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate is from 10 μg/cm² to 200 μg/cm²;
   (3) an area of the adhesive preparation is from 1 cm² to 25 cm²;
   (4) a thickness of the adhesive layer is from 20 μm to 120 μm;
   (5) a residual ratio of methyl 4-{[2((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate after storage at 40° C. for 1 month is 90% or more; and (6) a skin permeation rate ratio for a stratum corneum-removed skin to that for a normal skin is from 1 to 5.

15. The preparation according to claim 14, wherein the silicone adhesive is:
    [1] a mixture of a component (1): a linear or branched polydimethylsiloxane having a silanol group at a molecular chain end or in a side chain and a component (2): a polysilicate resin having a silanol group in the molecule;
    [2] a condensation reaction product of the component (1) and the component (2); or
    [3] a mixture of the mixture [1] and the condensation reaction product [2].

16. The preparation according to claim 15, wherein a viscosity of the component (1) at 25° C. is from 10 mPa·s to 100000 mPa·s and a weight average molecular weight of the component (2) in terms of styrene is from 500 to 100000.

17. The preparation according to claim 14 which is produced by mixing a solution having a viscosity of from 1000 mPa·s to 10000 mPa·s obtained by adding 50 to 1000 parts by mass of an aromatic hydrocarbon organic solvent, an aliphatic hydrocarbon organic solvent, an ester organic solvent, or a mixed solvent thereof to 100 parts by mass of the silicone adhesive with methyl 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoate as such or a mixture thereof with an aromatic hydrocarbon organic solvent, an aliphatic hydrocarbon organic solvent, an ester organic solvent, or a mixed solvent thereof.

18. A method of stabilizing a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid contained in a sustained release adhesive preparation, wherein a sustained release adhesive layer in the adhesive preparation contains two components, a C1-4 alcohol ester of 4-{[2-((1R,2R,3R)-3-hydroxy-2-{(1E,3S)-3-hydroxy-4-[3-(methoxymethyl)phenyl]but-1-enyl}-5-oxocyclopentyl)ethyl]sulfanyl}butanoic acid and a silicone adhesive.

* * * * *